United States Patent
Alshakhs

(10) Patent No.: US 11,066,911 B2
(45) Date of Patent: Jul. 20, 2021

(54) OPERATING HYDROCARBON WELLS USING MODELING OF IMMISCIBLE TWO PHASE FLOW IN A SUBTERRANEAN FORMATION

(71) Applicant: Saudi Arabian Oil Company, Dhahran (SA)

(72) Inventor: Mohammed Jawad A. Alshakhs, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 452 days.

(21) Appl. No.: 16/186,151

(22) Filed: Nov. 9, 2018

(65) Prior Publication Data

US 2019/0085673 A1 Mar. 21, 2019

Related U.S. Application Data

(63) Continuation-in-part of application No. 12/974,434, filed on Dec. 21, 2010, now abandoned.

(51) Int. Cl.
  *E21B 43/20* (2006.01)
  *G01N 33/28* (2006.01)
  (Continued)

(52) U.S. Cl.
  CPC ............ *E21B 43/20* (2013.01); *E21B 49/008* (2013.01); *G01N 33/24* (2013.01); *G01N 33/28* (2013.01)

(58) Field of Classification Search
  CPC ........ E21B 43/20; E21B 49/008; G01N 33/28
  See application file for complete search history.

(56) References Cited

U.S. PATENT DOCUMENTS 3,990,298 A   11/1976   Deans
4,158,957 A   6/1979   Deans et al.
(Continued)

FOREIGN PATENT DOCUMENTS

EP   1889999 A1   2/2008

OTHER PUBLICATIONS

Artus et al.; "Dynamics of the Water-Oil Front for Two-Phase, Immiscible Flow in Heterogeneous Porous Media. 1-Stratified Media" XP002423633, Transport in Porous Media, vol. 56, Jan. 1, 2004, pp. 283-303.
(Continued)

*Primary Examiner* — Alexander Satanovsky
(74) *Attorney, Agent, or Firm* — Bracewell LLP; Constance G. Rhebergen; Christopher L. Drymalla

(57) ABSTRACT

Provided are embodiments of operating an injection well of including partitioning a length of a sample of formation rock of the reservoir into length increments and determining (for a time increment) fluid saturations of the length increments based on fluid injected. The determining including, for each length increment, determining a volume of fluid injected into, fractional flow of fluid produced from, and a fluid saturation for the length increment during the time increment. The method including determining whether the volume of the fluid injected is saturated into the length of the sample during the time increment, and if so determining a flood front saturation model for the reservoir based on the fluid saturations and a fluid injection rate corresponding to the flood front saturation model, and operating the injection well according to the fluid injection rate.

16 Claims, 9 Drawing Sheets

(51) Int. Cl.
*E21B 49/00* (2006.01)
*G01N 33/24* (2006.01)

(56) References Cited

U.S. PATENT DOCUMENTS

| | | | |
|---|---|---|---|
| 6,052,520 A | | 4/2000 | Watts, III |
| 2006/0047432 A1* | | 3/2006 | Egermann ............ G01N 33/241 |
| | | | 702/12 |
| 2008/0046223 A1* | | 2/2008 | Noetinger ............... E21B 43/16 |
| | | | 703/9 |
| 2008/0167849 A1 | | 7/2008 | Hales et al. |
| 2009/0319242 A1* | | 12/2009 | Lee ......................... E21B 43/00 |
| | | | 703/10 |
| 2010/0057413 A1 | | 3/2010 | Lee et al. |
| 2010/0312535 A1 | | 12/2010 | Chen et al. |

OTHER PUBLICATIONS

Buckley, S. et al., "Mechanism of Fluid Displacement in Sands", Trans. AIME (1942) vol. 146: 107-116.
Cardwell, W.T.: "The Meaning of the Triple Value in Noncapillary Buckley-Leverett Theory," Trans. AIME (1959), vol. 216: 271-276.
Dake, L. P.: "Practice of Reservoir Engineering, Elsevier", Amsterdam, 2001. pp. 345-350.
International Search Report and Written Opinion for International Application No. PCT/US2011/062015 (SA679/PCT); International Filing date Nov. 23, 2011; Report dated Aug. 22, 2012 (pp. 1-11).
Vuckovie, J.: "The Error in Buckley-Leverett Frontal Theory", SPE7193, 1978.
Welge, H. J.: "A Simplified Method of Computing Oil Recovery by Gas or Water Drive", Trans. AIME (1952) vol. 195: 91-98.

\* cited by examiner

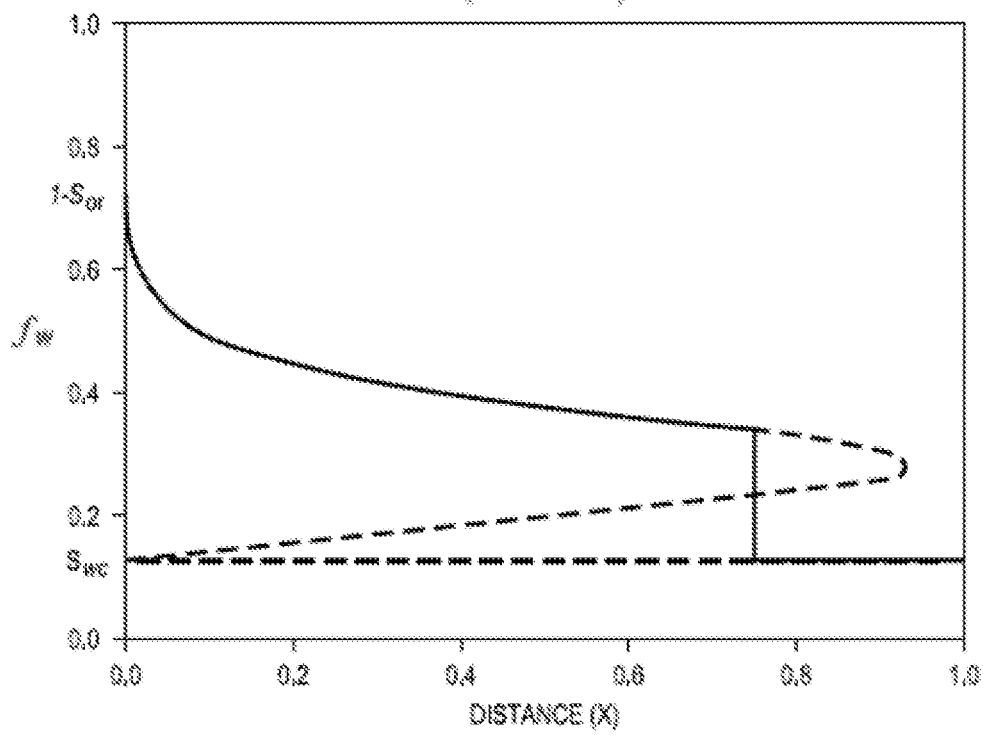
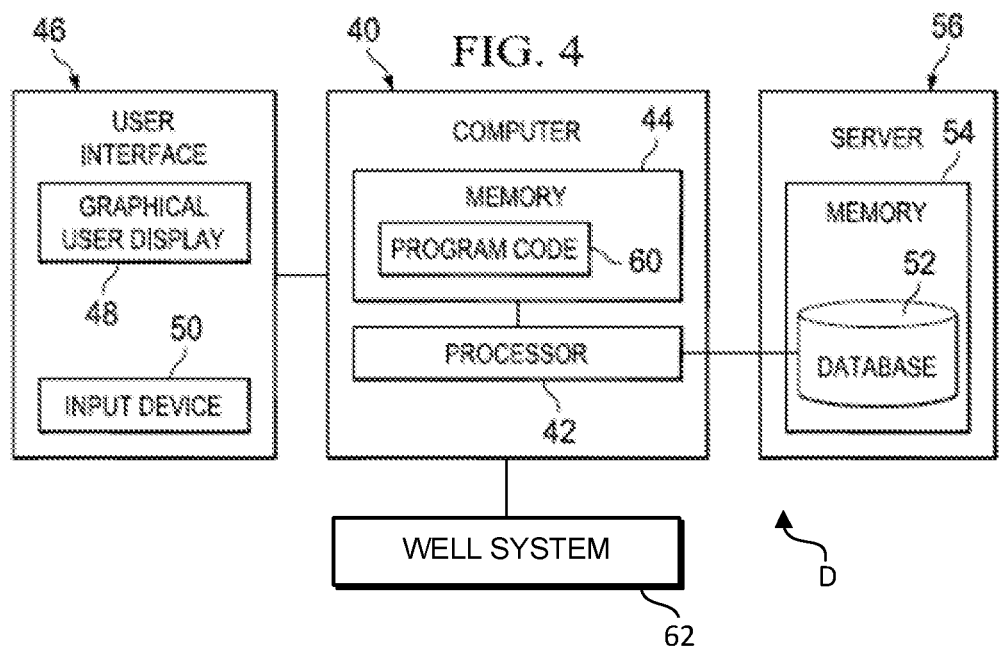

OPERATING HYDROCARBON WELLS USING MODELING OF IMMISCIBLE TWO PHASE FLOW IN A SUBTERRANEAN FORMATION

RELATED APPLICATIONS

This application is a continuation-in-part of U.S. patent application Ser. No. 12/974,434 titled "MODELING IMMISCIBLE TWO PHASE FLOW IN A SUBTERRANEAN FORMATION" and filed Dec. 21, 2010, which is hereby incorporated by reference in its entirety.

BACKGROUND

1. Field

The described embodiments relate to computerized subterranean reservoir analysis, and in particular to forming models of the flow of two immiscible fluid phases for core sample permeability testing and for reservoir simulation and development.

2. Description of the Related Art

It has been conventional practice at some time during the production life of a subsurface hydrocarbon formation to increase production by recovery techniques. Among such techniques is the injection of water. Water and oil are immiscible, in that they do not mix with each other or chemically react with each other. The flow rates through the formation rock sands of the fluids present in the reservoirs (oil, gas and water) as a rule also differ for the different fluids.

During the life of the reservoir, it has been typical practice to form models or simulations of the flow of these fluids through the reservoir. This was done in order to accurately evaluate and analyze the potential or historic production from the reservoir. A common practice in the industry is use to finite difference simulation that is derived from mass conservation laws, fluid phase behavior, and Dacy's fluid flow approximation. This simulation is referred to here as conventional simulation.

In forming models or simulations of reservoir fluid flow, the behavior of the immiscible fluids had to be taken into account. A model known as the Buckley Leverett model has been widely used for a number of years. This technique was originally described in "Mechanism of Fluid Displacement in Sands", S. E. Buckley and M. C. Leverett, Trans. AIME (1942), Vol. 145, p. 107 -116. Over the ensuing years, there have been certain problems noted in the literature with this method. A specific problem is that the formation fluid saturation values produced with the Buckley Leverett method indicated multiple values of fluid saturation for the same physical location, which by definition cannot occur.

SUMMARY

Briefly, the described embodiments provide a new and improved methods of obtaining a measure of saturation of a porous media segment of earth formation rock to an injected volume of fluid, and applying the measure of saturation to enhance production of hydrocarbons from a reservoir. In some embodiments, a length of a system sample of the porous media segment is partitioned into a number of sample length increments, and a measure is formed of the volume of injected fluid injected into a sample length increment during a selected increment of time. A measure is then formed of fractional flow of fluid produced in the sample length increment by the injected fluid during the selected time increment, and a measure formed of the fluid saturation for the injected fluid in the sample length increment during the selected time increment. A record is then made of the measure of the of the fluid saturation for the injected fluid in the sample length increment during the selected time increment, and a measure formed of the remaining volume of the fluid not saturated into the sample length increment during the selected time increment.

In some embodiments, fluid saturations determined using the techniques described here are used to enhance production of hydrocarbons from a reservoir. For example, in the case of a reservoir having injection and production wells, simulations can be run to determine fluid saturations and corresponding advancements of injection fluid through the reservoir at different fluid injection rates, an injection rate or production rate that maximizes production from the reservoir may be determined based on the simulations, and the injection or production wells can be operated at the determined injection or production rates, respectively. In the case of a multi-layer reservoir such techniques can be employed to facilitate even advancement of injection fluid through the different reservoir layers. For example, simulations can be run to determine fluid saturations and corresponding advancements of injection fluid through the different layers of the reservoir at different fluid injection rates, injection rates or production rates for each of the layers that promote even advancement of the fluid through the different layers (e.g. (for example), to inhibit premature water breakthrough at the production wells and maximize production from the production wells) may be determined based on the simulations, and the injection and production wells can be operated at the determined injection and production rates, respectively, for the different layers which can in turn promote maximized production from the reservoir. In an illustrative embodiment, oil production may be enhanced by reducing injection rates or production rates for layers that exhibit relatively fast injection fluid advancement, or increasing injection rates or production rates for layers that exhibit relatively slow injection fluid advancement.

Applicant has also recognized that the described techniques require less data input in comparison to conventional simulation techniques, which can save time and costs over conventional simulation and well operating techniques. For example, the described embodiments of simulation are based on the following input data: relative permeability, injection rates, and grid porosity. In comparison, conventional simulation techniques often require this input data in addition to permeability properties of grids, injection pressure, production pressure and reservoir pressure. Accordingly, the described techniques may be accomplished without having to invest time and money into determining the additional data.

Applicant has also recognized that the described techniques provide improved results in comparison to conventional techniques, which can in turn enhance hydrocarbon production from a reservoir. For example, the described embodiments may not be susceptible to additional errors and uncertainties introduced in the additional data employed by conventional simulation techniques. If the permeability of a layer is under estimated, for example, a conventional simulation may depict an unrealistically slow injection fluid advancement which can result in increasing an injection rate. This increase can lead to an undesirably high rate of injection fluid advancement and premature injection fluid breakthrough at a production well, which can in turn reduce hydrocarbon production from the well. Notably, described embodiments are not dependent on permeability and thus are not susceptible to inaccurate estimates of permeability, injection pressure, production pressure or reservoir pressure.

As a further example, the described embodiments are relatively less sensitive to grid size than conventional simulations which are susceptible to calculation errors that arise from gridding. For example, in conventional simulation a relatively small/fine gird size leads to higher resolution of the injection fluid advancement but can introduce more calculation errors, while the alternative relatively large/course grid size can result in poor resolution. In described embodiments, the distance between an injection location and a production location (e.g., between an injection well and a production well) and grid size are converted to dimensionless quantities in the simulation. This facilitates field-scale simulation using the same dimensionless gird size as for simulation of laboratory experiments, without introducing additional errors.

The described embodiments also provide a new and improved data processing system for forming a measure of saturation of a porous media segment of earth formation rock to an injected volume of fluid, and applying the measure of saturation to enhance production of hydrocarbons from a reservoir. The data processing system comprises a data storage memory and a processor which performs the steps of partitioning a length of a system sample of the porous media segment into a number of sample length increments, and forming a measure of the volume of injected fluid injected into a sample length increment during a selected time increment. The processor also forms a measure of fractional flow of fluid produced in the sample length increment by the injected fluid during the selected time increment and a measure of the fluid saturation for the injected fluid in the sample length increment during the selected time increment. The processor also forms a record in the data storage memory of the measure of the of the fluid saturation for the injected fluid in the sample length increment during the selected time increment, and forms a measure of the remaining volume of the fluid not saturated into the sample length increment during the selected time increment. Such a system may be employed to enhance production of hydrocarbons from a reservoir using the fluid saturations determined in manner similar to that described here.

The described embodiments further provide a new and improved data storage device which has stored in a computer readable medium computer operable instructions for causing a data processing system to form a measure of saturation of a porous media segment of earth formation rock to an injected volume of fluid, and applying the measure of saturation to enhance production of hydrocarbons from a reservoir. The instructions stored in the data storage device causing the data processing system to partition a length of a system sample of the porous media segment into a number of sample length increments, and form a measure of the volume of injected fluid injected into a sample length increment during a selected time increment. The instructions stored in the data storage device include instructions causing the data processing system to form a measure of fractional flow of fluid produced in the sample length increment by the injected fluid during the selected time increment, and a measure of the fluid saturation for the injected fluid in the sample length increment during the selected time increment. The instructions stored in the data storage device also include instructions causing the data processing system to form a record for storage in the data processing system of the measure of the of the fluid saturation for the injected fluid in the sample length increment during the selected time increment, and further to form a measure of the remaining volume of the fluid not saturated into the sample length increment during the selected time increment. The instructions may be further executable to use the fluid saturations determined to enhance production of hydrocarbons from a reservoir by employing techniques similar to those described here.

Provided in some embodiments is a method of operating an injection well of a hydrocarbon reservoir. The method including: partitioning a length of a sample of formation rock of the hydrocarbon reservoir into a given number of length increments; determining, for a selected time increment, fluid saturations of the length increments based on fluid injected into the length of the sample including: for each length increment of the length increments: determining a volume of fluid injected into the length increment of the sample during the selected time increment; determining fractional flow of fluid produced from the length increment of the sample by the fluid injected into the length increment of the sample during the selected time increment; and determining a fluid saturation for the length increment attributable to the fractional flow of fluid produced and the fluid injected that is saturated into the length increment of the sample during the selected time increment; determining, based on the fluid saturations of the length increments of the sample during the selected time increment, whether the volume of the fluid injected is saturated into the length of the sample during the selected time increment; and in response to determining that the volume of the fluid injected is saturated into the length of the sample during the selected time increment: determining, based on the fluid saturations determined, a flood front saturation model for the hydrocarbon reservoir; determining a fluid injection rate corresponding to the flood front saturation model for the hydrocarbon reservoir; and operating the injection well to inject fluid into the reservoir at the fluid injection rate.

In some embodiments, the fluid injection rate corresponds to the volume of fluid injected into the length increment of the sample during the selected time increment. In certain embodiments, the sample of formation rock of the hydrocarbon reservoir includes a core sample extracted from the hydrocarbon reservoir. In some embodiments, the injected fluid includes water. In certain embodiments, the sample of formation rock of the hydrocarbon reservoir includes a first sample of formation rock of a first layer of the hydrocarbon reservoir and the flood front saturation profile for the hydrocarbon reservoir includes a first flood front saturation profile for first layer of the hydrocarbon reservoir, where operating the injection well to inject fluid into the reservoir at the fluid injection rate includes operating the injection well to inject fluid into the first layer of the reservoir at the fluid injection rate, the method further including: determining a second flood front saturation profile for a second layer of the hydrocarbon reservoir; determining a second fluid injection rate corresponding to the second flood front saturation profile for the second layer of the hydrocarbon reservoir; and operating an injection well to inject fluid into the second layer of the reservoir at the second fluid injection rate. In certain embodiments, the method includes, in response to determining that the volume of the fluid injected is not saturated into the length of the sample during a selected time increment, determining, for a second time increment, second fluid saturations of the length increments based on fluid injected into the length of the sample for a second selected time increment, where the flood front saturation model for the hydrocarbon reservoir is determined based on the second fluid saturations.

Provided in some embodiments is a non-transitory computer readable storage medium including program instructions stored thereon that are executable by a processor to cause the operations of the method of operating an injection well of a hydrocarbon reservoir described previously.

Provided in some embodiments is a system that includes the following: a reservoir flood front simulation system adapted to: partition a length of a sample of formation rock of the hydrocarbon reservoir into a given number of length increments; determine, for a selected time increment, fluid saturations of the length increments based on fluid injected into the length of the sample including: for each length increment of the length increments: determining a volume of fluid injected into the length increment of the sample during the selected time increment; determining fractional flow of fluid produced from the length increment of the sample by the fluid injected into the length increment of the sample during the selected time increment; and determining a fluid saturation for the length increment attributable to the fractional flow of fluid produced and the fluid injected that is saturated into the length increment of the sample during the selected time increment; determine, based on the fluid saturations of the length increments of the sample during the selected time increment, whether the volume of the fluid injected is saturated into the length of the sample during the selected time increment; and in response to determining that the volume of the fluid injected is saturated into the length of the sample during the selected time increment: determine, based on the fluid saturations determined, a flood front saturation profile for the hydrocarbon reservoir; and determine a fluid injection rate corresponding to the flood front saturation profile for the hydrocarbon reservoir; and a well system including an injection well adapted to inject fluid into the reservoir at the fluid injection rate responsive to the determination of the fluid injection rate by the reservoir flood front simulation system.

In some embodiments, the fluid injection rate corresponds to the volume of fluid injected into the length increment of the sample during the selected time increment. In certain embodiments, the sample of formation rock of the hydrocarbon reservoir includes a core sample extracted from the hydrocarbon reservoir. In some embodiments, the injected fluid includes water. In certain embodiments, the sample of formation rock of the hydrocarbon reservoir includes a first sample of formation rock of a first layer of the hydrocarbon reservoir and the flood front saturation profile for the hydrocarbon reservoir includes a first flood front saturation profile for first layer of the hydrocarbon reservoir, where the injection well is adapted to inject fluid into the first layer of the reservoir at the fluid injection rate responsive to the determination of the fluid injection rate by the reservoir flood front simulation system, the reservoir flood front simulation system further adapted to: determine a second flood front saturation profile for a second layer of the hydrocarbon reservoir; determine a second fluid injection rate corresponding to the second flood front saturation profile for the second layer of the hydrocarbon reservoir; and the injection well further adapted to inject fluid into the second layer of the reservoir at the second fluid injection rate responsive to the determination of the second fluid injection rate by the reservoir flood front simulation system. In some embodiments, the reservoir flood front simulation system further adapted to, in response to determining that the volume of the fluid injected is not saturated into the length of the sample during a selected time increment, determine, for a second selected time increment, second fluid saturations of the length increments based on fluid injected into the length of the sample for a second time increment, where the flood front saturation profile for the hydrocarbon reservoir is determined based on the second fluid saturations.

Provided in some embodiments is a method of operating an injection well based on a model of fluid saturation as a function of length within a porous media segment of earth formation rock of a reservoir during flow through the porous media segment of a volume of a fluid injected into the porous media segment at an initial time to form immiscible oil and water fluid phases. The method including the steps of: (a) partitioning a length of a sample of the porous media segment into a number of sample length increments; (b) forming a measure of a volume of water injected into a sample length increment during a selected time increment; (c) forming a measure of fractional flow of fluid produced in the sample length increment of the porous media segment by the injected water during the selected time increment; (d) forming a measure of the fluid saturation for the injected water in the sample length increment of the porous media segment during the selected time increment; (e) forming a record of the measure of the fractional flow of fluid produced and the measure of the fluid saturation for the injected water in the sample length increment of the porous media segment during the selected time increment; (f) forming a measure of the remaining volume of the injected water not saturated into the sample length increment of the porous media segment during the selected time increment; (g) determining whether measures of the fluid saturation for the injected water have been formed for each sample length increment of the porous media segment during the selected time increment, and (h) if not, selecting a next adjacent sample length increment of the porous media segment during the selected time increment, and returning to the steps of forming a measure of the fractional flow of fluid produced and forming a measure of the fluid saturation for the injected fluid for the next adjacent sample length increment of the porous media segment; (i) and, if so, determining whether the formed measure of remaining volume of the injected water during the selected time increment indicates presence of a remaining volume of water for injection into an adjacent length sample increment of the porous media segment; (j) if so, incrementing the selected time increment to a new selected time increment and repeating the steps of forming a measure of fractional flow of fluid, forming a measure of the fluid saturation, forming a record of the measure of the of the fluid saturation, and forming a measure of the remaining volume of the injected water not saturated for injection into the adjacent sample length increment of the porous media segment during the selected time increment; and (k) if not, forming a model of the fluid saturation for the injected water as a function of the length of the porous media segment in response to the volume of water injected, the model of the fluid saturation indicating different flow rate behavior of the immiscible oil and water phases during the injecting of water into the porous media segment; and (l) determining a fluid injection rate corresponding to the model of the fluid saturation; and (m) operating the injection well to inject fluid into the reservoir at the fluid injection rate.

BRIEF DESCRIPTION OF THE DRAWINGS

FIG. 3 is graphical display of a measure of shock front water saturation profile as a function of non-dimensional distance formed from the set of data used for the display of FIG. 1 using the prior art Buckley Leverett model corrected by the utilization of average water saturation.

FIG. 4 is a schematic diagram of a computer system for modeling fluid flow for subsurface earth formations according to one or more embodiments.

DETAILED DESCRIPTION

Figure 1:
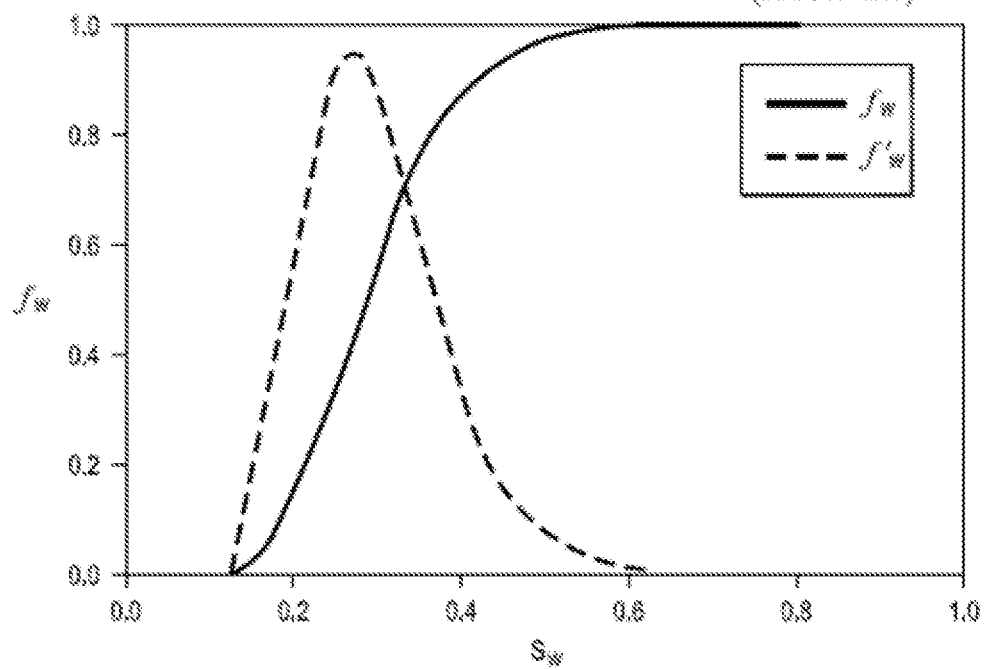
FIG. 1 is a graphical display of a measure of fractional flow profile as a function of water saturation.

At the outset, an explanation of the physical aspects and relationships of two phase fluid flow is provided. A model known as the Buckley Leverett model was derived based on the presence of certain physical conditions for the model. The fluid displacement is one dimensional, and conditions are at equilibrium. Fluid pressure is maintained, and the fluids are immiscible. Gravity and capillary pressures are deemed negligible, and the fluids are incompressible. FIG. 1 is a graphical display of a synthetic fractional flow profiles as a function of saturation, which is typically generated from laboratory experiments on a core sample of formation rock. Notably FIG. 1 is an example plot of a fractional fluid flow profile $f_w$ and its derivative $f'_w$ as a function of water saturation $S_w$. This input data is used to give an ideal output profile of the prior art Buckley Leverett model method.

For a displacement process where water displaces oil, the fractional flow of water at any point in a core plug or reservoir is defined as:

$$f_w = \frac{q_w}{q_w + q_o} \quad \text{Equation (1)}$$

where $q_w = \dfrac{kk_{rw}A\frac{\Delta p_w}{\Delta L}}{\mu_w}$ and $q_o = \dfrac{kk_{ro}A\frac{\Delta p_o}{\Delta L}}{\mu_o}$ $$\Rightarrow f_w = \frac{\dfrac{kk_{rw}A\frac{\Delta p_w}{\Delta L}}{\mu_w}}{\dfrac{kk_{rw}A\frac{\Delta p_w}{\Delta L}}{\mu_w} + \dfrac{kk_{ro}A\frac{\Delta p_o}{\Delta L}}{\mu_o}}$$

where,
$f_w$ is the fractional flow of water,
k is the permeability,
$k_{rw}$ is relative permeability for the water phase,
$k_{ro}$ is relative permeability for the oil phase,
A is the cross-sectional area of the core (porous medium),
$\Delta p_w$ is the pressure drop across the water phase,
$\Delta p_o$ is the pressure drop across the oil phase,
$\Delta L$ is the length of the core (porous medium),
$\mu_w$ is the water viscosity, and
$\mu_o$ is the oil viscosity.

Assuming that the pressure gradients in the water and oil are similar and neglecting capillary pressure effects, the prior equation becomes:

$$\Rightarrow f_w = \frac{1}{1 + \dfrac{\mu_w}{\mu_o}\dfrac{k_{ro}}{k_{rw}}} \quad \text{Equation (2)}$$

With the application of a mass balance of water around a control volume of length for a certain period of time, the mass balance can be written as:

$$[(q_w\rho_w)_x - (q_w\rho_w)_{x+\Delta x}]\Delta t = A\Delta x\phi[(S_w\rho_w)_{t+\Delta t} - (S_w\rho_w)_t] \quad \text{Equation (3)}$$

where,
$q_w$ is the volumetric water flow rate,
$\rho_w$ is the water density,
x is the distance,
$\Delta x$ is the incremental length,
$\phi$ is the porosity,
$S_w$ is the water saturation,
t is the time, and
$\Delta t$ is the time step.

Assuming that the water is incompressible, the prior equations become:

$$[(q_w)_x - (q_w)_{x+\Delta x}]\Delta t = \quad \text{Equation (4)}$$

$$A\Delta x\phi[(S_w)_{t+\Delta t} - (S_w)_t] \Rightarrow \frac{\Delta x}{\Delta t} = \frac{1}{A\phi}\frac{[(q_w)_x - (q_w)_{x+\Delta x}]}{[(S_w)_{t+\Delta t} - (S_w)_t]}$$

If $\Delta x \to 0$ and $\Delta t \to 0$ and substituting the flow rates in Equation (3) by the fractional flow term from Equation (1), the conventional known Buckley Leverett equation model is:

$$\frac{dx}{dt} = \frac{q}{A\phi} \frac{df_w}{dS_w} \qquad \text{Equation (5)}$$

where, $$\frac{dx}{dt}$$

is the velocity of moving front described in terms of change in distance over change in time in the fluid direction,
q is the flow rate,
$\phi$ is the porosity,
$df_w$ is the change in the water fractional flow, and
$dS_w$ is the water saturation change.

The integration of Equation (4) has the following form which describes the flood front advancement:

$$X = \frac{qt}{A\phi} \frac{df_w}{dS_w} \qquad \text{Equation (6)}$$

where X is a distance of flood front advancement over a length of time.

To plot the flood front using Buckley Leverett model, $$\frac{df_w}{dS_w} \text{ or } f'_w$$

can be calculated from the fractional flow curve that is generated from the relative permeability using Equation (2) and then back substituting the values in Equation (6). As noted previously, FIG. 1 is an example plot of a fractional fluid flow profile $f_w$ and its derivative $f'_w$ as a function of water saturation $S_w$.

Figure 2:
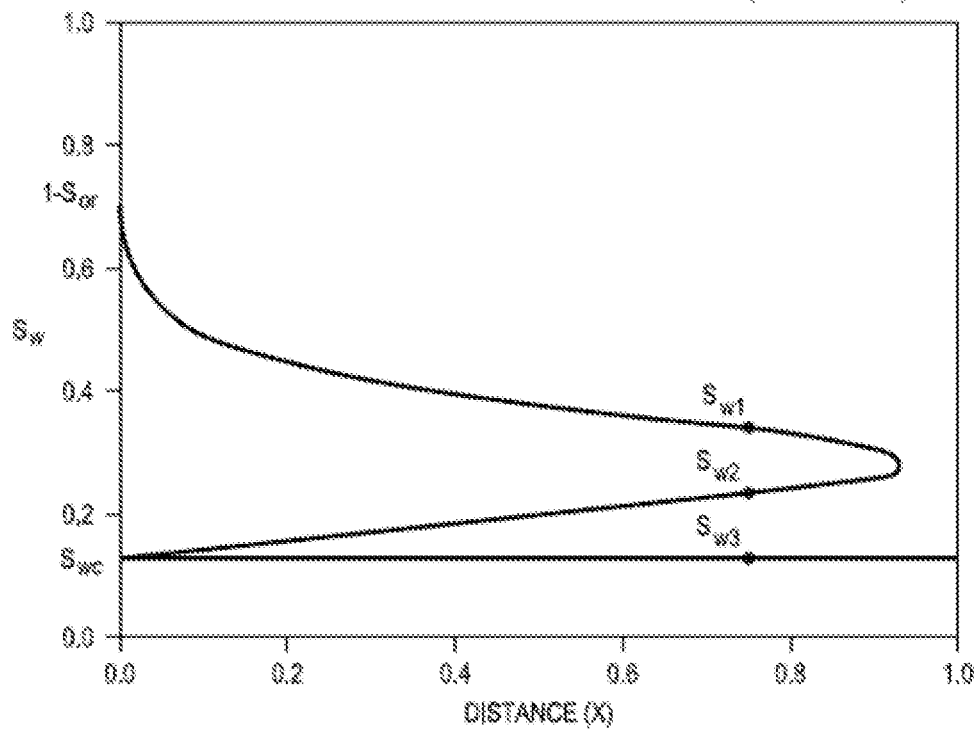
FIG. 2 is a graphical display of a measure of water flood saturation as a function of non-dimensional distance formed from the set of data used for the display of FIG. 1 using the prior art Buckley Leverett model without applying any correction.

By applying the original Buckley Leverett model, as is evident from FIG. 2, the computed water saturation profile has three saturations values at any distance, i.e. (that is), $S_{w1}$, $S_{w2}$ and $S_3$ (or $S_{wc}$). The Buckley Leverett model was modified and a shock front saturation introduced to add a realistic meaning to the original model plotted in FIG. 2. The connate water saturation line prior to the shock front and most of the saturation curve derived from the Buckley Leverett equation were eliminated and replaced by the shock front (FIG. 3). The mathematical solution for the front was derived later by others utilizing the concept of average water saturation.

As is evident from FIG. 2, the Buckley Leverett model provides multiple saturations at each point along the distance plot, which is physically impossible. It has been proposed by others that this problem with the Buckley Leverett model resides in the relative permeability functions.

The Buckley Leverett model is a representation of a mass balance for a system at equilibrium conditions. The model indicates in the accumulation of the displacing fluid for a certain time interval (or "time increment") (e.g., defined by the time from t to t+$\Delta$t), the change in saturation is equal to the difference of the displacing fluid volume entering the system to the one exiting the system, as shown in Equation (4). This indicates that $f_w'$ is expressed as:

$$\frac{[(q_w)_x - (q_w)_{x+\Delta x}]}{[(S_w)_{t+\Delta t} - (S_w)_t]} = \qquad \text{Equation (7)}$$

$$\frac{[(f_w)_x - (f_w)_{x+\Delta x}]}{[(S_w)_{t+\Delta t} - (S_w)_t]} \text{ where } q_w \text{ in dimensionless form}$$

$$\Rightarrow \frac{[(f_w)_x - (f_w)_{x+\Delta x}]_{t+\Delta t}}{[(S_w)_{t+\Delta t} - (S_w)_t]} =$$

$$\frac{df_w}{dS_w} = f'_w \text{ when } \Delta x \to 0 \text{ and } \Delta t \to 0$$

Notably, the preceding equations describe $f_w'$ generated from physical/mathematical derivation. The expression in Equation 8 describes $f_w'$ of FIG. 1 that is generated from experimental core flood data.

With the described embodiments, it has been determined that the errors in the flood front advancement calculations discussed previously are because the models were not implemented correctly. The $f_w'$ used in the calculation of the front (Equation 7) is not the same physical object as $f_w'$ which is obtained from the Buckley Leverett model. The $f_w'$ of FIG. 1 (illustrating $f_w'$ calculated from experimental data) is generated from data measured during relative permeability experiments in laboratory testing, which do not consider the inlet injected volume in the generation of the fractional flow curve (FIG. 1). In mathematical terms, the $f_w'$ of FIG. 1 can be expressed as:

$$\frac{[(q_w)_{t+\Delta t} - (q_w)_t]}{[(S_w)_{t+\Delta t} - (S_w)_t]} = \frac{[(f_w)_{t+\Delta t} - (f_w)_t]}{[(S_w)_{t+\Delta t} - (S_w)_t]}, \qquad \text{Equation (8)}$$

where $q_w$ in dimensionless form $$\Rightarrow \frac{[(f_w)_{t+\Delta t} - (f_w)_t]_{x+\Delta x}}{[(S_w)_{t+\Delta t} - (S_w)_t]} =$$

$$\frac{df_w}{dS_w} = f'_w \text{ when } \Delta x \to 0 \text{ and } \Delta t \to 0$$

where $(f_w)_t$ is the water fractional flow at time (t).

Thus, it can be seen that the $f_w'$ in Equation (8) is not the same $f_w'$ as that in Equation (7). The first one accounts for the change in rate at the outlet of a system while the second one accounts for the difference of the rate between the inlet and the outlet points of a system. The $f_w'$ in Equation (7) also violates the equilibrium assumptions of Buckley Leverett because the rates at the inlet and the outlet should not change with time. The physical meaning of the solution when using the incorrect $f_w'$ is that the accumulation of the displacing fluid for a certain time interval inside a system is equal to change of the produced volumes of that fluid, which cannot physically occur.

It can thus be demonstrated that the values of $f_w'$ cannot be taken directly from the fractional flow curves derived from the relative permeability experiment and applied to Buckley Leverett model, due to inconsistency in the physical meaning. The described embodiments provide a model with a new and improved approach for modeling a flood front saturation profile in earthen rock where $f_w'$ can be used directly in the model without any inconsistencies. Equation (6) can be expressed in the correct form according to the described embodiments as:

$$1 = \frac{qt}{XA\phi} \frac{[(f_w)_x - (f_w)_{x+\Delta x}]}{[(S_w)_{t+\Delta t} - (S_w)_t]} \quad \text{Equation (9)}$$

Equation 9 illustrates how the $$\frac{df_w}{dS_w}$$

from Equation 6 is expressed using $f_w$ and $S_w$ terms.

For a water flooding system that has an injection point and a production point, and $t_0=0$, the Equation (9) can be re-written as:
where $$1 = \frac{q\Delta t}{XA\phi} \frac{[(f_w)_i - (f_w)_p]}{[(S_w)_{\Delta t} - (S_{wi})]} \quad \text{Equation (10)}$$

$(f_w)_i$ is the fractional flow at the injection point (inlet),
$(f_w)_p$ is the fractional flow at the production point (outlet),
$(S_w)_{\Delta t}$ is the water saturation at time $\Delta t$, and
$S_{wi}$ is the initial water saturation (water saturation at t=0).

Since both the numerator and denominator represent the same system, the factor should represent the dimensionless pore volume of water injected into the system ($PV_i$):

$$\frac{q\Delta t}{XA\phi} = PV_i \quad \text{Equation (11)}$$

By substituting Equation (11) into Equation (10), the equation becomes:

$$1 = PV_i \frac{[(f_w)_i - (f_w)_p]}{[(S_w)_{\Delta t} - (S_{wi})]} \quad \text{Equation (12)}$$

To track down the forward propagation of the front as fluid is being injected into a system of known fractional flow curve, the system should be divided into subsystems of a fixed $\Delta x$. The fractional flow curve should be known and the fractional flow curve should be plotted against the average water saturation.

The unknown parameters in this equation for each $\Delta x$ are $(f_w)_p$ and $(S_w)_{\Delta t}$. The injected water ratio $(f_w)_i$ and the initial water saturation prior to injection $(S_{wi})$ are fixed parameters that can be measured easily. The pore volume injected ($PV_i$) is a variable that is a function of time and can be obtained using Equation (11). This will leave two unknowns, $(f_w)_p$ and $(S_w)_{\Delta t}$. The values of the unknowns can be found by utilizing the fraction flow curve to find the appropriate values that can satisfies the equation.

The same technique can be used for the backward tracking of the flood front. In this case, $(f_w)_p$ and $(S_w)_{\Delta t}$ are fixed known parameters, while $(f_w)_i$ and $(S_{wi})$ are the unknowns and should be solved for using the fractional flow curves. The described embodiments use the foregoing analysis in forming models of fluid flow in computerized analysis of subterranean reservoirs and rock formations, based on porous media segments or samples.

As illustrated in FIG. 4, a data processing system D according to the described embodiments includes a computer 40 having a processor 42 and memory 44 coupled to the processor 42 to store operating instructions, control information and database records therein. The computer 40 may, if desired, be a portable digital processor, such as a personal computer in the form of a desktop computer, a laptop computer, or notebook computer. It should also be understood that the computer 40 may be a multicore processor with nodes such as those from Intel Corporation or Advanced Micro Devices (AMD), or a mainframe computer of any conventional type of suitable processing capacity such as those available from International Business Machines (IBM) of Armonk, N.Y.

The computer 40 has a user interface 46 and an output display 48 for displaying output data or records of processing of well logging data measurements performed according to the described embodiments to obtain a measure of transmissibility of fluid in subsurface formations. The output display 48 includes components such as a printer and an output display screen capable of providing printed output information or visible displays in the form of graphs, data sheets, graphical images, data plots and the like as output records or images.

The user interface 46 of computer 40 also includes a suitable user input device or input/output control unit 50 to provide a user access to control or access information and database records and operate the computer 40. Data processing system D further includes a database 52 stored in computer memory, which may be internal memory 44, or an external, networked, or non-networked memory as indicated at 54 in an associated database server 56.

The data processing system D includes program code 60 stored in memory 44 of the computer 40. The program code 60, according to the described embodiments may be in the form of computer operable instructions causing the data processor 42 to form obtain a measure of transmissibility of fluid in subsurface formations, as will be set forth. The memory 44 may be non-transitory computer readable memory having the program code 60 stored thereon, with the program code 60 comprising computer executable program instructions. The program instructions may be executable by the processor 42 of the computer 40 to cause the computer to perform the operation described here, including, for example, the operations relating to determining measures of saturation and corresponding flood front saturation profiles (e.g., described with regard FIG. 5) and applying the measures of saturation and corresponding flood front saturation profiles to enhance production of hydrocarbons from a reservoir (e.g., described with regard to FIGS. 12 and 13). This can include, for example, executing simulations to determine fluid saturations and corresponding flood front saturation profiles representing corresponding advancement of injection fluid through the reservoir at different fluid injection rates, determining an injection rate or production rate that maximizes production from the reservoir based on the results of the simulations, and controlling injection or production wells to operate at the determined injection and production rates, respectively. In some embodiments, the computer 40 provides operational control of a well system 62. For example, the computer 40 may control the well system 62 to operate one or more injection or production wells in a hydrocarbon reservoir to operate at determined injection or production rates, respectively.

It should be noted that program code 60 may be in the form of microcode, programs, routines, or symbolic computer operable languages that provide a specific set of ordered operations that control the functioning of the data processing system D and direct its operation. The instructions of program code 60 may be may be stored in memory 44 of the computer 40, a data storage device having a computer usable medium stored thereon (e.g., a computer diskette, magnetic tape, conventional hard disk drive, electronic read-only memory, or optical storage device, or a data storage device such as server 54.

Figure 5:
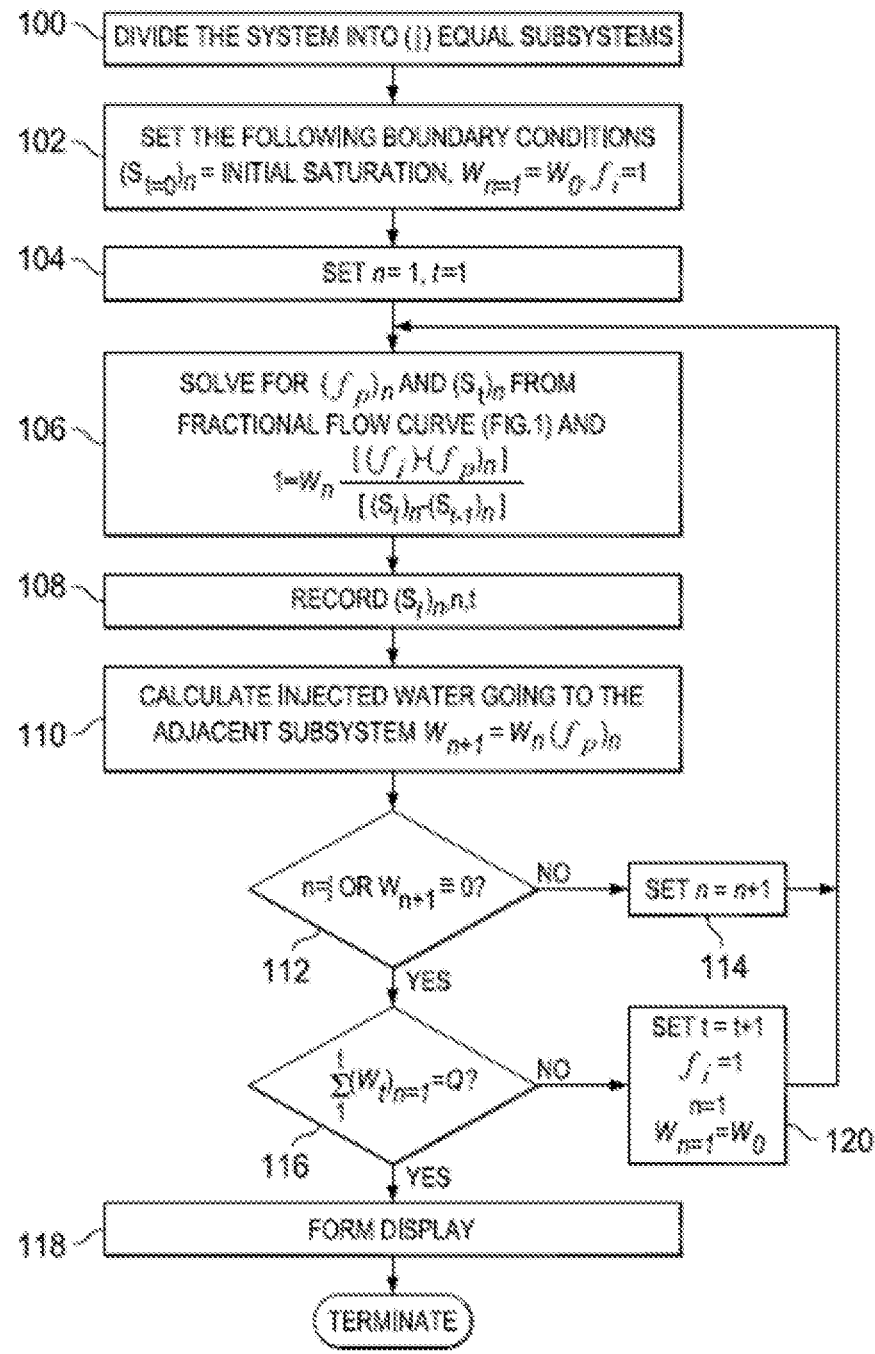
FIG. 5 is functional block diagram of a set of data processing steps performed in the computer system of FIG. 4 during the forming of fluid flow models for subsurface earth formations according to one or more embodiments.

FIG. 5 is a flowchart that illustrates a method of forming a measure of saturation of porous media segments of earth formation rock to an injected volume of fluid. The operations of method of FIG. 5 may be performed by the computer 40 or another operator of the well, for example. The input data to processing system D are laboratory or other data including the initial water saturation values, system length, porosity, injected volume and ratio data, and data regarding fractional flow curves (or relative permeability of formation rock samples to oil and to water).

For a porous media segment or system that follows Buckley Leverett conditions and has a fluid, such as water, that is being injected to displace another fluid, such as oil, the flow can be described by the following relationship:

$$1 = (W_t)_n \frac{[(f_i) - (f_p)_n]}{[(S_t)_n - (S_{t-1})_n]} \quad \text{Equation (13)}$$

Where:
n: the subsystem or length increment number among increments in the segment, which is equal to 1 at the injecting point
t: the time step of injection, which is equal to 0 prior to injection
$W_n$: Volume of fluid injected in the subsystem n at time step t
$f_i$: Fractional flow of the injected fluid
$(f_p)_n$: Fractional flow of the produced fluid
$(S_t)_n$: Saturation of injected fluid at the increment or subsystem n
$(S_{t-1})_n$: Saturation of the injected fluid at the increment or subsystem n in the previous time step.
Q: Total volume of fluid injected.

The water saturation $S_w$ can be determined as a function of time and one-dimension space in the segment by the applying the method described and which is illustrated schematically in the process sequence of FIG. 5. During step 100, the length of the porous media segment or sample is be divided in the computer data into (n) smaller subsystems of equal length, and the total volume injected is allocated in the computer data into smaller volumes. The discretization of the volumes injected should represent the volume injected during a time step such that $$Q = \sum_{1}^{t} (W_t)_{n=1} \quad \text{Equation (13)}$$

The injected water ratio $(f_i)$, the initial water saturation prior to injection $(S_{t=0})$ and the injected volume $(W_t)_{n=1}$ are known parameters that can be experimentally measured. As indicated at step 102, these initial parameters are provided as input data for use in further processing.

During step 104, initial counts are set for processing to be performed for the first length increment located at injection point for the first time step, where n=1, t=1.

During step 106, the fractional flow of the produced fluid $(f_p)$ and the saturation of the injected fluid $(S_t)_n$ at the length increment n should be found by utilizing the pre-determined fraction flow curve (the solid line of FIG. 6, notably there are no units in the y-axis because these terms are dimensionless) to find the appropriate values of $(f_p)$ and $(S_t)_n$ that satisfy Equation 13. This can be done in several ways, such as by using a conventional computer numerical solution method such as the Newton's method or by other computerized optimization or iterative trial and error method. During step 108, the determined values for fractional flow and saturation of the injected fluid for the present length increment n are stored in memory.

During step 110, the values of $(f_p)$ and $(S_t)_n$ at the current length increment n are used for material balance computations to find what remaining volume that is available to be injected in the adjacent subsystem by applying the following equation: $W_{n+1} = W_n (f_p)_n$ During step 112, a decision is made based on whether volume injected in the adjacent time step $(W_{n+1})$ is not equal to zero. If such is the case, this means that there is still some fluid to flow into the next adjacent length increment n+1. In this event, during step 114, the length n is incremented and the values of $(f_p)$ and $(S_t)_n$ are to be found for the adjacent length increment and processing continues by returning to step 106.

If the subsystem number n is equal to j, it means that the saturation was measured for all the subsystems at the specified time step. If volume injected in the adjacent time step $(W_{n+1})$ is indicated equal to zero during step 112, then the total injected volume injected at the specified time step t has entered into the previous length increments, and no more mobile fluid is left to enter the next adjacent length increment. The flood front saturation profile can be obtained for the whole sample at that time step t by plotting $(S_t)_n$ of the length increments 1 through n as a function of distance.

During step 116, a decision is made based on whether the cumulative volume injected in the length increment is equal to the total volume injected in the segment. If this is so indicated, further processing should terminate and the saturation profiles determined may be plotted as indicated in step 118. The flood front saturation profiles determined may be displayed as a function of time and space in one-dimension by way of the graphical user display 48, for example. If during step 116 the cumulative fluid injected does not yet equal the total volume injected, the time interval counter t is increased during step 120.

For determining the saturation profile at the next time step, $(W)_t$ is equal to the injected volume during this time step, and the $(S_{t-1})_n$ is equal to the $(S_t)_n$ from the previous time step.

The processing is performed for the next time step using the volume of water injected during that time step and processing returns to step 106 for continued data value determinations. This iterative process may be continued until it is determined that the cumulative volume injected in the length increment is equal to the total volume injected in the segment at step 116.

Figure 6:
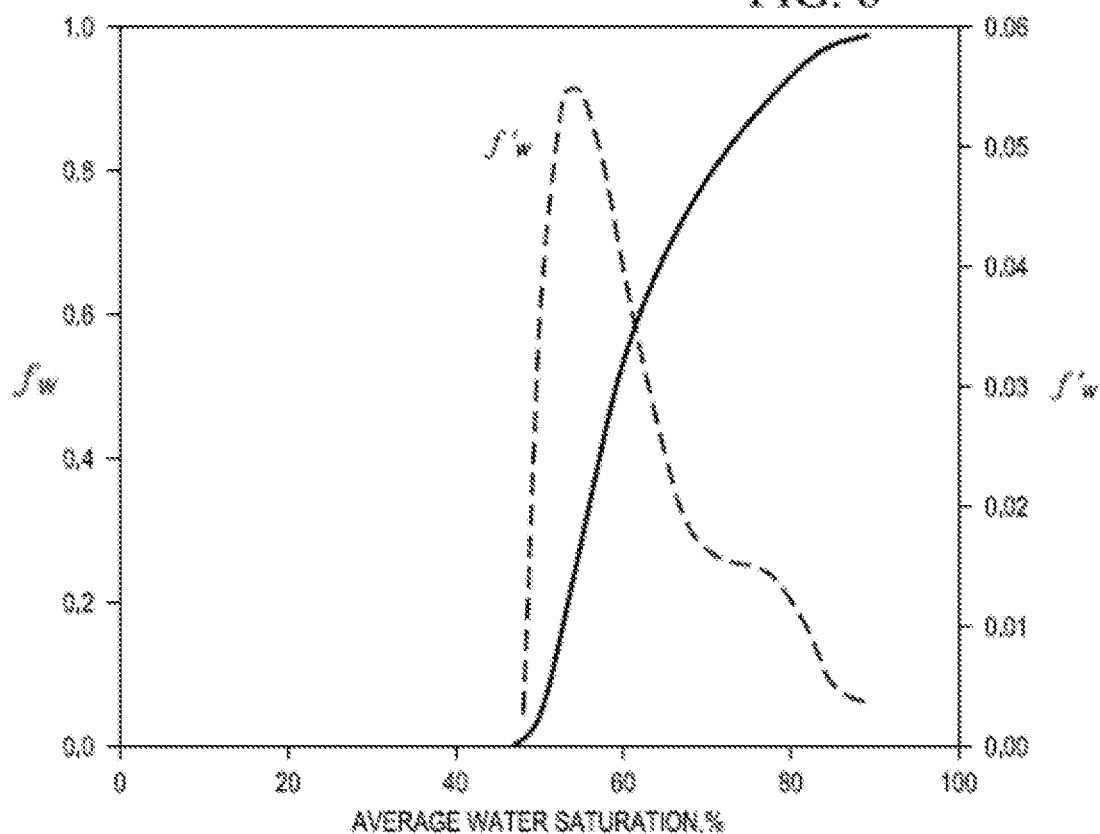
FIG. 6 is a graphical display of a synthetic typical example of fractional flow profile of an injected fluid as a function of water saturation.
Figure 7:
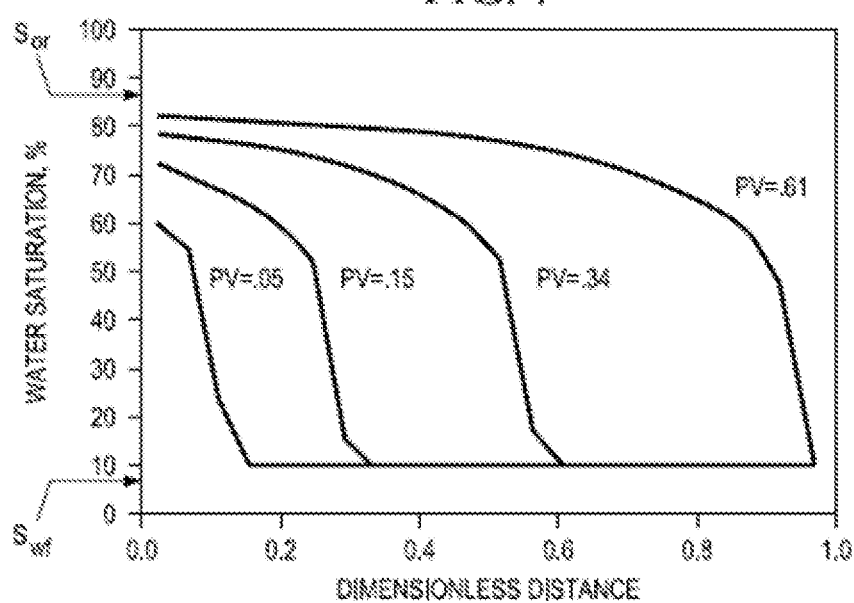
FIG. 7 is a graphical display of a measure of water saturation profile as a function of non-dimensional distance formed from the data set used for the display of FIG. 6 for various pore volume (PV) ratios according to one or more embodiments.

FIG. 6 illustrates an example display of the input used for forward tracking of a flood front according to the described embodiments. It is typically generated from laboratory experiments on a core sample of formation rock. In this example, the data was generated from steady state core-flood experiments. The core length was chosen to be Δx and has a dimensionless length. The processing was carried out to see the behaviour of the flood front for a segment that was assumed to have similar petrophysical properties to the entire core. The processing was carried out for different amounts of pore volumes and the front advancement was tracked down until the saturation reached the initial connate water saturation of the sample. Unlike a conventional Buckley Leverett front model, the solution for each front plotted in FIG. 7 is unique and no multiple values were generated. It is also clear the shock front phenomenon appears in the front without any need to enforce it in the plot to match reality.

The flood front saturation profile of FIG. 7 indicates a pore volume (PV) ratio determined with reference to largest core volume. The PV ratio is based on the pore volume of the segment that has a dimensionless distance of 1 unit.

Figure 8:
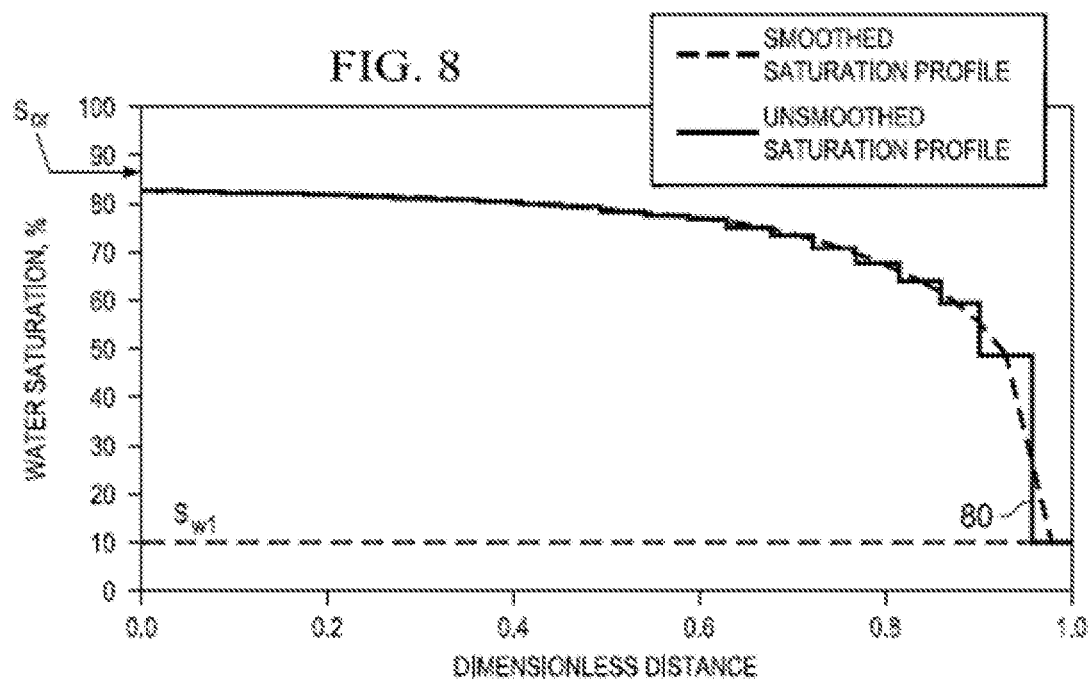
FIG. 8 is a graphical display of measures of water saturation profile as a function of non-dimensional distance formed from the data set used for the display of FIG. 6 before and after data smoothing techniques are applied according to one or more embodiments.

The saturation profiles plotted in FIG. 7 are displayed as actual values for each successive length increment but can also be smoothed compared to the actual calculated increment values. The present technique forms a model of water saturation based on actual saturation of a very small $\Delta x$ length increment of the sample. In the plot of FIG. 7, the $\Delta x$ increment was arbitrarily chosen to be the length of the core and the values were used to honor the saturation only at the middle of step of $\Delta x$ to smooth the curves. The shape of the original, unsmoothed curve compared to the smoothed one is shown on FIG. 8. It should be noted that the marked differences between determined model saturation profile values at each successive length in the data plot can be avoided by selection of a very small $\Delta x$ length increment.

Figure 9:
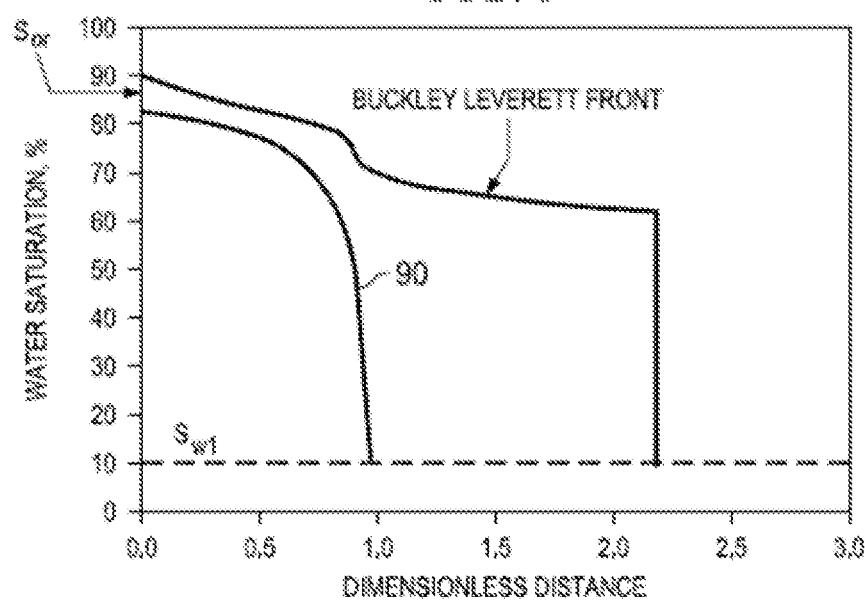
FIG. 9 is a graphical display of comparison plots of measures of saturation profile formed from the data set used for the display of FIG. 6 from synthetic data and from the prior art Buckley Leverett method.

A comparison was conducted between saturation profile proposed by Buckley Leverett with one according to the described embodiments is shown in FIG. 9. The same amount of volume injected was used in both schemes of front calculation (dimensionless volume=0.61). The dimensionless distance here refers to the core length.

A simple visual comparison between the two curves reveals certain things. The Buckley Leverett front model of FIG. 9 does not show the same volume of water injected compared to the original volume used in the calculation of the front movement. The area under the front curve and above the initial saturation line should represent the dimensionless volume of water injected. The area under the Buckley Leverett front model of FIG. 9 shows that the volume injected is 1.59, which is not equal to the injected volume of 0.61, which was used as an input to the model. This indicates clearly that Buckley Leverett frontal model violates material balance rules. The front plotted from the method of the described embodiments shows an injected volume of 0.61, which is similar to one used in the front movement calculations.

The Buckley Leverett front model of FIG. 9 shows an inflection point at a distance equal to 1. This is because the front is sensitive to changes in derivative of the fractional flow curve while the front model according to the described embodiments is not.

Figure 10:
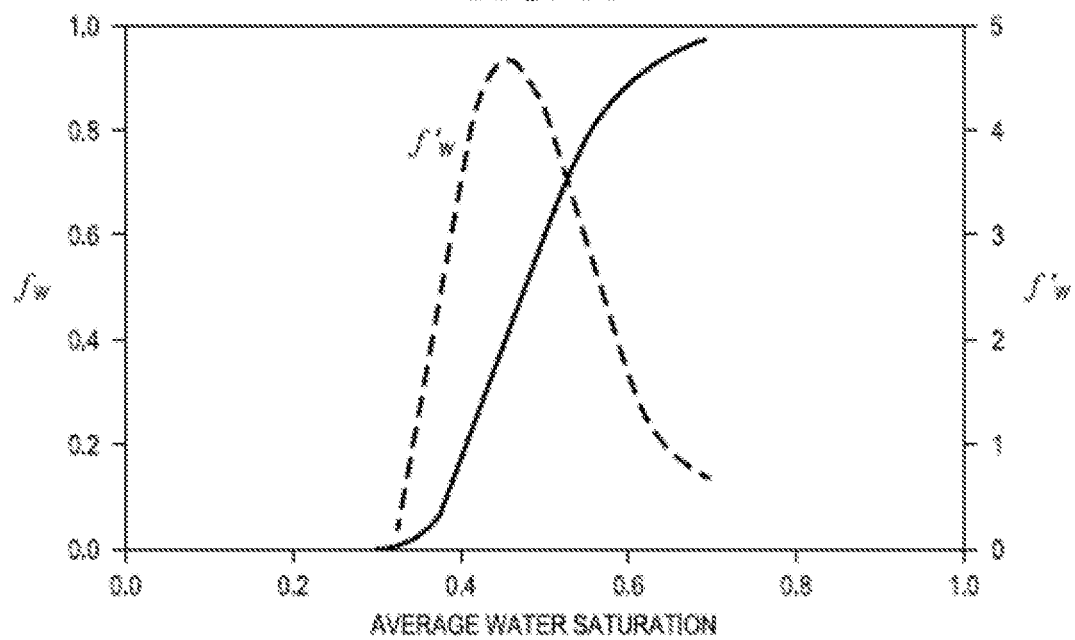
FIG. 10 is a graphical display of synthetic fractional flow profiles as a function of saturation.
Figure 11:
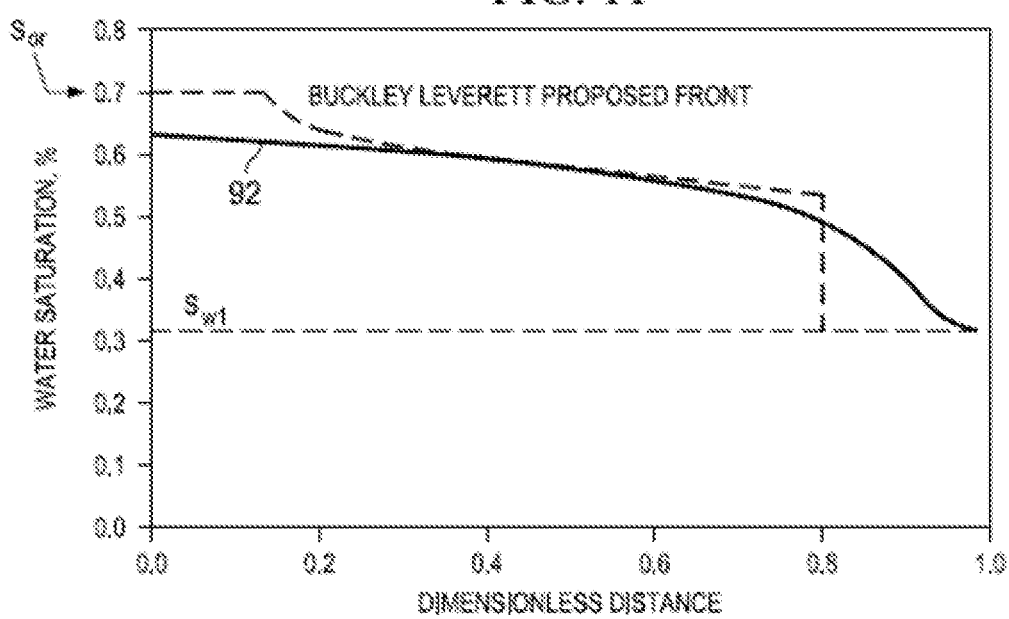
FIG. 11 is a graphical display of synthetic fractional flow profiles as a function of saturation.

The conventional Buckley Leverett front model and the front model formed according to the described embodiments were also examined for a synthetic data set that best suited the Buckley Leverett front model. The suitability of the data in this context refers to a conventional monotonic shape of the derivate, since that may reduce many errors in the conventional Buckley Leverett front model. FIG. 10 shows the synthetic fractional flow data and saturation front if injected in a core. A comparison between the models is shown in FIG. 11 where the described embodiments demonstrate a well developed smoother realistic shock front (right side of the curves) while Buckley Leverett model show a sharp shock front represented by a straight line, which is an artefact introduced by Weldge modification to the Buckley Leverett model. This artefact is well known in the prior art but was not modelled smoothly except for the described embodiments.

Another important difference between the models output of FIG. 11 is on the left side of the curves. The described embodiments demonstrate a more realistic estimate of $S_{or}$ when compared to the Buckley Leverett model. This is because the Buckley Leverett model sets the first few points directly to $S_{or}$ while the described embodiments assign high oil saturation values at a slower and gradual rate. The described embodiments better matche reality because reaching the $S_{or}$ value is not an easy process as could be indicated from Buckley Leverett model.

In some embodiments, fluid saturations determined using the techniques described here are used to enhance production of hydrocarbons from a reservoir. For example, in the case of a reservoir having injection and production wells, simulations can be run to determine fluid saturations and corresponding flood front saturation profiles representing corresponding advancement of injection fluid through the reservoir at different fluid injection rates, an injection rate or production rate that maximizes production from the reservoir may be determined based on the simulation results (e.g., including the flood front saturation profiles), and the injection wells or production wells can be operated at the determined injection or production rates, respectively. For example, a simulation similar that described with regard to FIG. 5 may be run to determine a flood front saturation profile that extends through the formation of a reservoir (e.g., from an injection well and toward a production well) for a given fluid injection rate. The injection rate may be used to determine the cumulative injected volume for each time step in the simulation. For example, an injection rate of 1,000 cubic meters ($m^3$) per day may result in a determination of injected volumes of 1,000 $m^3$, 2,000 $m^3$ and 3000 $m^3$ for respective time steps of 1 day, 2 days, 3 days and so forth. Generation of a simulation may include completing the process of FIG. 5 for some or all of the time steps to generate a flood front saturation profile for each of some or all of the time steps, and a generating simulation that includes the flood front saturation profiles generated to illustrate the advancement of the flood front of the injected fluid over time. For example, a simulation may include a flood front saturation profile at days 1, 2, 3 and so forth based on the injection rate of 1,000 cubic meters. If it is determined that the advancement of the flood front of the injected fluid over time is suitable, the injection well may be operated at the corresponding injection rate. For example, if it is determined that the advancement of the flood front of the injected fluid over time determined for the injection rate of 1,000 $m^3$ per day is suitable, the injection well may be operated at the injection rate of 1,000 $m^3$. If it is determined that the advancement of the flood front of the injected fluid over time is not suitable, the simulation may be repeated based on a modified injection rate. For example, if it is determined that the advancement of the flood front of the injected fluid over time determined for the injection rate of 1,000 $m^3$ per day is too fast or too slow, the simulation may be repeated based on a modified injection rate of 900 $m^3$ per day or 1,100 $m^3$ per day, respectively. In some embodiments, the assessment may be repeated for any number of different injection rates, and the injection well may be operated at an injection rate that corresponds to the most suitable advancement of the flood front of the injected fluid over time. For example, the assessment may be repeated for injection rates of 500-1,500 $m^3$ per day (in increments of 100 $m^3$ per day), and if the advancement of the flood front of the injected fluid over time determined for the injection rate of 1,000 m³ per day is the most suitable profile, the injection well may be operated at an injection rate of 1,000 m³ per day.

Figure 12:
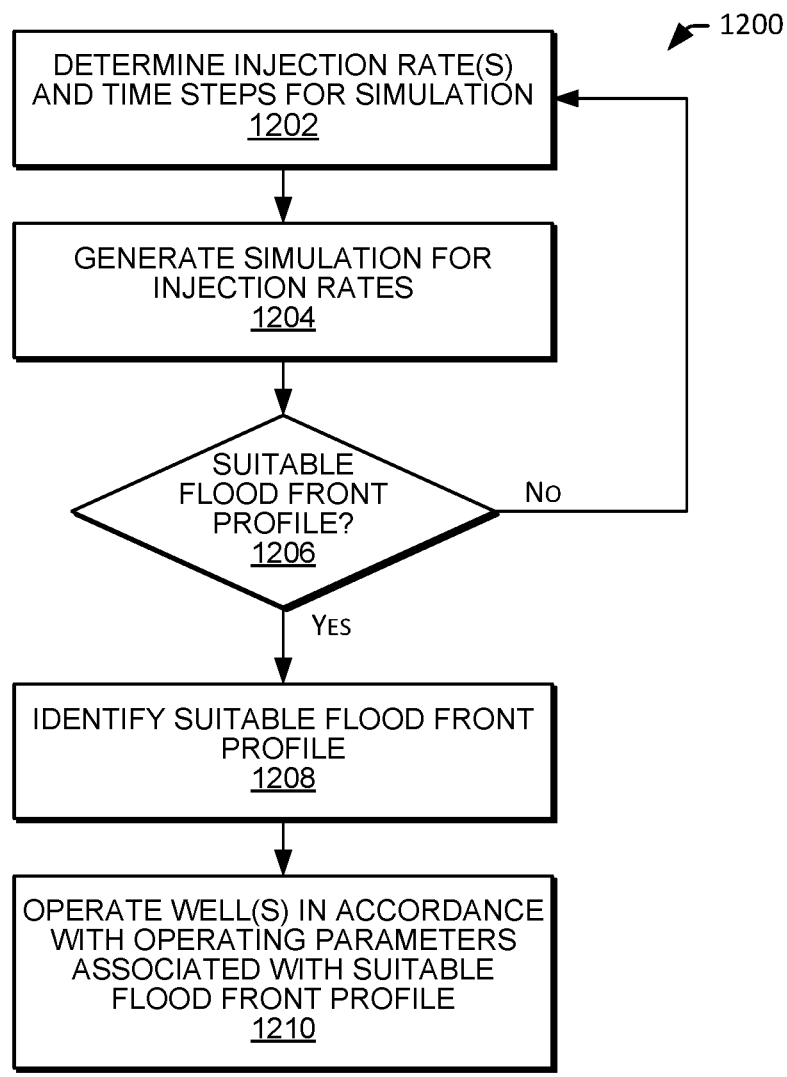
FIG. 12 is a flowchart diagram that illustrates a method of operating a well based on determined flood front advancement according to one or more embodiments.

FIG. 12 is a flowchart that illustrates a method 1200 of operating a well based on determined flood front advancement in accordance with one or more embodiments. The operations of method 1200 may be performed by the computer 40 or another operator of the well, for example.

In some embodiments, method 1200 includes determining one or more injection rates and time steps for simulation (block 1202). This can include, for example, determining injection rates of 500 m³ per day, 600 m³ per day, 700 m³ per day . . . and 1,500 m³ per day and time steps of 1 year, 2 years, 3 years . . . and 20 years.

In some embodiments, method 1200 includes generating a simulation for each injection rate (block 1204). This can include generating a simulation that includes, for each injection rate, determining a corresponding simulation that includes a determined flood front saturation profile at each of the time steps. Continuing with the previous example, this may include (e.g., using the techniques described with regard to FIG. 5) for a first injection rate of 500 m³ per day, determining a first simulation that includes a determined flood front saturation profile at each of years 1-20 based on the first injection rate of 500 m³ per day, for a second injection rate of 600 m³ per day, determining a second simulation that includes a determined flood front saturation profile at each of years 1-20 based on the second injection rate of 600 m³ per day, and so forth for each of the injection rates up to 1,500 m³ per day.

In some embodiments, method 1200 includes determining whether a suitable flood front saturation profile is identified (1206). Method 1200 may include, if a suitable flood front saturation profile has not been identified, proceeding to identify a new set of injection rates (block 1202) and repeating the process (blocks 1204-1206) using the new set of injection rates. For example, if all of resulting simulations indicate flood front saturation profiles that exhibit an undesirably fast flood front advancement (e.g., a flood front advancement that exceeds a threshold rate of advancement), a new set of relatively lower injection rates of 100 m³ per day, 200 m³ per day, 300 m³ per day, 400 m³ per day and 500 m³ per day may be identified and the process may be repeated for the new set of relatively low injection rates.

Method 1200 may include, if a suitable flood front saturation profile is identified, proceeding to identifying a most suitable flood front saturation profile (block 1208) and operating one or more wells in accordance with operating parameters corresponding to the most suitable flood front saturation profile (block 1210). For example, if injection rates of 900 m³ per day, 1,000 m³ per day, and 1,100 m³ per day all exhibit acceptable rates of flood front advancement (e.g., a flood front advancement that falls within an acceptable range of rate of advancement) with 1,100 m³ per day exhibiting a most suitable flood front saturation profile (e.g., a flood front that maximizes production from the reservoir), a corresponding injection well may be controlled to operate at the injection rate of 1,100 m³ per day (e.g., the injection well may be operated to inject water into the reservoir at a rate of at or near 1,100 m³ per day). In such an embodiment, the injection fluid may urge production (e.g., hydrocarbons such as oil and gas) toward one or more production wells, which are operated to extract (or "produce") the production from the reservoir.

The operations of method 1200 may be repeated over the life of a well to operate based on updated reservoir information. For example, method 1200 may be performed at the time the injection well is created, two years after the injection well is created when a second/updated set of data for the well and formation is available, five years after the injection well is created when a third/updated set of data for the well and formation is available, and so forth.

In the case of a multi-layer reservoir such techniques can be employed to facilitate even advancement of injection fluids through the different reservoir layers. For example, simulations can be run to determine fluid saturations and corresponding flood front saturation profiles representing corresponding advancements of injection fluid through the different layers of the reservoir at different combinations of fluid injection rates, injection rates or production rates for each of the layers that promotes even advancement of the fluid through the different layers (e.g., to inhibit premature water breakthrough at the production wells and maximize production from the production wells) may be determined based on the simulation results (e.g., including the flood front saturation profiles), and the injection or production wells can be operated at the determined injection or production rates, respectively, for the different layers which can in turn promote maximized production from the reservoir. In an illustrative embodiment, oil production may be enhanced by reducing injection rates and production rates for reservoir layers that exhibit relatively fast injection fluid advancement, or increasing injection rates or production rates for layers that exhibit relatively slow injection fluid advancement.

Figure 13:
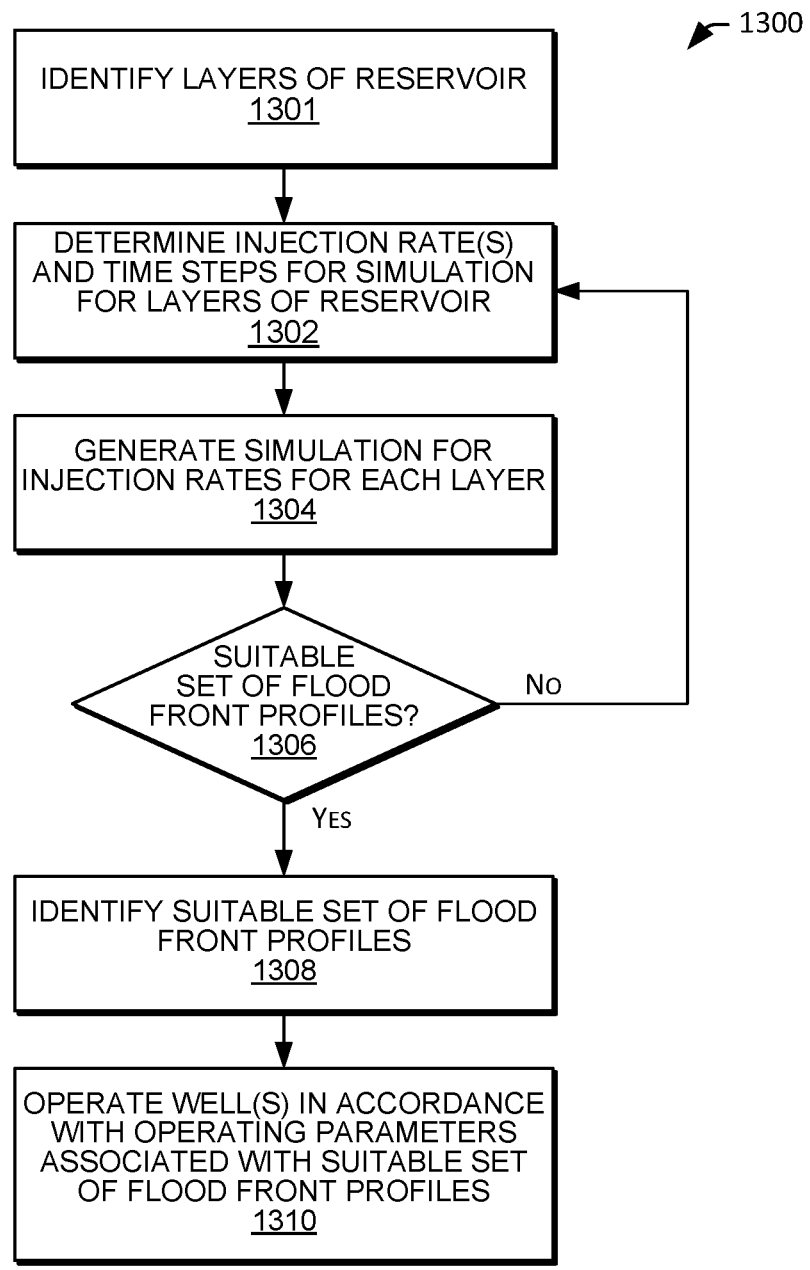
FIG. 13 is a flowchart that illustrates a method of operating a well in a multi-layer reservoir based on determined flood front advancements according to one or more embodiments.

FIG. 13 is a flowchart that illustrates a method 1300 of operating a well in a multi-layer reservoir based on determined flood front advancements in accordance with one or more embodiments. The operations of method 1300 may be performed by the computer 40 or another operator of the well, for example.

In some embodiments, method 1300 includes identifying different layers of a reservoir that are expected to exhibit flood front advancement (block 1301). This can include for example, identifying first, second, and third layers of a reservoir that extend between an injection well and a production well.

In some embodiments, method 1300 includes for each of the layers, determining one or more injection rates and time steps for simulation (block 1302). This can include, for example, determining injection rates of 500 m³ per day, 600 m³ per day, 700 m³ per day . . . and 1,500 m³ per day and time steps of 1 year, 2 years, 3 years . . . and 20 years for each of the three layers.

In some embodiments, method 1300 includes generating, for each layer, a simulation for each injection rate (block 1304). This can include generating, for each of the three layers, a simulation that includes determining, for each injection rate, a corresponding simulation that includes a determined flood front saturation profile at each of the time steps. Continuing with the previous example, this may include (e.g., using the techniques described with regard to FIG. 5) for a first injection rate of 500 m³ per day, determining, for each of the three layers, a first simulation that includes a determined flood front saturation profile at each of years 1-20 based on the first injection rate of 500 m³ per day, for a second injection rate of 600 m³ per day, determining a second simulation that includes a determined flood front saturation profile at each of years 1-20 based on the second injection rate of 600 m³ per day, and so forth for each of the injection rates up to 5,000 m³ per day.

In some embodiments, method 1300 includes determining whether a suitable set of flood front saturation profiles for the layers is identified (1306). Method 1300 may include, if a suitable set of flood front saturation profiles for the layers has not been identified, proceeding to identify a new set of injection rates (block 1302) and repeating the process (blocks 1304-1306) using the new set of injection rates. For example, if all of the resulting simulations indicate flood front saturation profiles that exhibit an undesirably fast flood front advancement (e.g., a flood front advancement that exceeds a threshold rate of advancement), a new set of relatively lower injection rates of 100 $m^3$ per day, 200 $m^3$ per day, 300 $m^3$ per day, 400 $m^3$ per day and 500 $m^3$ per day may be specified for each of the layers and the process may be repeated for the new set of relatively lower injection rates. As a further example, if none of the resulting simulations indicate flood front saturation profiles with relatively similar (or "even") rates of flood front advancement for all three of the layers (e.g., having flood front advancement rates within about 10% of one another), a new set of injection rates for one or more of the layers may be specified and the process may be repeated for the new set of relatively lower injection rates. Injection rates may be increased, decreased or maintained for layers with flood front saturation profiles that exhibit relatively slow, fast or moderate flood front advancement. For example, if all of the flood front saturation profiles for the first layer exhibit relatively slow flood front advancement, all of the flood front saturation profiles for the second layer exhibit relatively fast flood front advancement, and all of the flood front saturation profiles for the third layer exhibit relatively moderate flood front advancement, the new sets of injection rates may include relatively higher injection rates of 5,000 $m^3$ per day, 5,100 $m^3$ per day, 5,200 $m^3$ per day, 5,300 $m^3$ per day and 5,400 $m^3$ per day for the second layer relatively lower injection rates of 100 $m^3$ per day, 200 $m^3$ per day, 300 $m^3$ per day, 400 $m^3$ per day and 500 $m^3$ per day for the second layer, and maintained injection rates for the third layer.

Method 1300 may include, if a set of suitable flood front saturation profiles is identified, proceeding to identify a most suitable set of flood front saturation profiles (block 1308) and operating one or more wells based on operating parameters corresponding to the most suitable set of flood front saturation profiles (block 1310). For example, if injection rates of 900 $m^3$ per day, 1,000 $m^3$ per day, and 1,100 $m^3$ per day all exhibit acceptable rates of flood front advancement for the first layer, injection rates of 1,200 $m^3$ per day, 1,300 $m^3$ per day, and 1,400 $m^3$ per day all exhibit acceptable rates of flood front advancement for the second layer, and injection rates of 700 $m^3$ per day, 800 $m^3$ per day, and 900 $m^3$ per day all exhibit acceptable rates of flood front advancement for the third layer, with the combination of 900 $m^3$ per day for the first layer, 1,3000 $m^3$ per day for the second layer, and 700 $m^3$ per day for the third layer, exhibiting a most suitable combination of flood front saturation profiles for the layers (e.g., a set of flood fronts that exhibit relatively even rates of advancement (e.g., having flood front advancement rates within about 10% of one another) such that the flood fronts of the three layers would reach a producing well at or near the same time, and in turn facilitate maximizing production from the reservoir), one or more corresponding injection wells may be controlled to operate to maintain injection rates of 900 $m^3$ per day for the first layer, 1,300 $m^3$ per day for the second layer, and 700 $m^3$ per day for the third layer (e.g., an injection well may be operated to inject water into the first layer of the reservoir at a rate of at or near 900 $m^3$ per day, to inject water into the second layer of the reservoir at a rate of at or near 1,300 $m^3$ per day, and to inject water into the third layer of the reservoir at a rate of at or near 700 $m^3$ per day). In such an embodiment, the injected fluids may urge production (e.g., hydrocarbons such as oil and gas) toward one or more production wells, which are operated to extract (or "produce") the production from the reservoir.

Figure 14A:
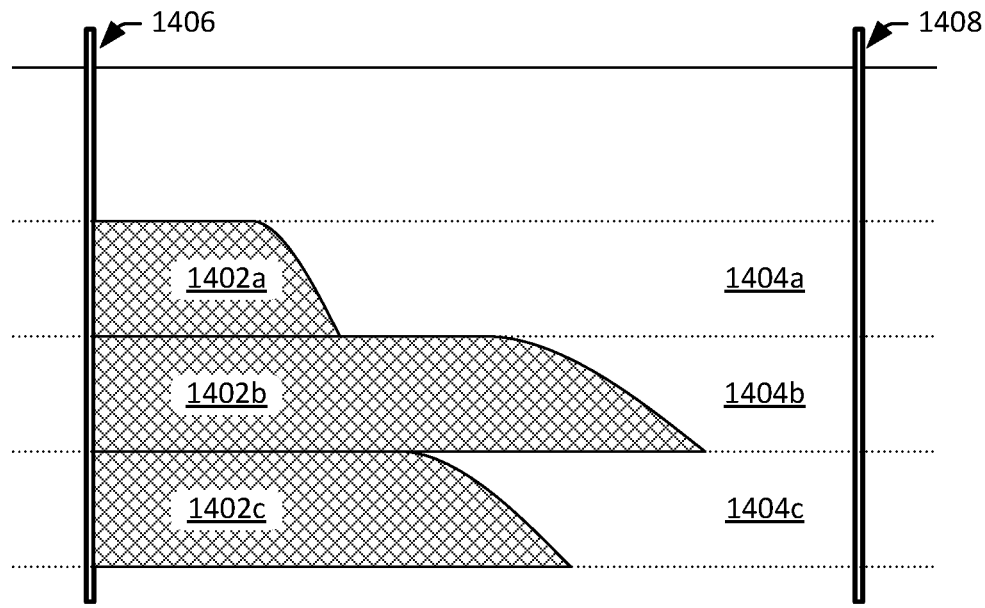
FIG. 14A is a diagram that illustrates relatively uneven advancement of flood front saturation profiles in multiple reservoir layers.

FIG. 14A is a diagram that illustrates relatively uneven advancement of flood front saturation profiles in multiple reservoir layers in accordance with one or more embodiments. In the illustrated embodiment, the first flood front saturation profile 1402a indicates that injected fluid (indicated by the shaded area) is advancing (e.g., from an injection location, such as an injection well 1406, to a production location, such as a production well 1408) at a relatively slow rate in the first/upper layer 1404a, the second flood front saturation profile 1402b indicates that injected fluid is advancing at a relatively fast rate in the second/middle layer 1404b, and the third flood front saturation profile 1402c indicates that injected fluid is advancing at a moderate rate in the third/lower layer 1404c.

Figure 14B:
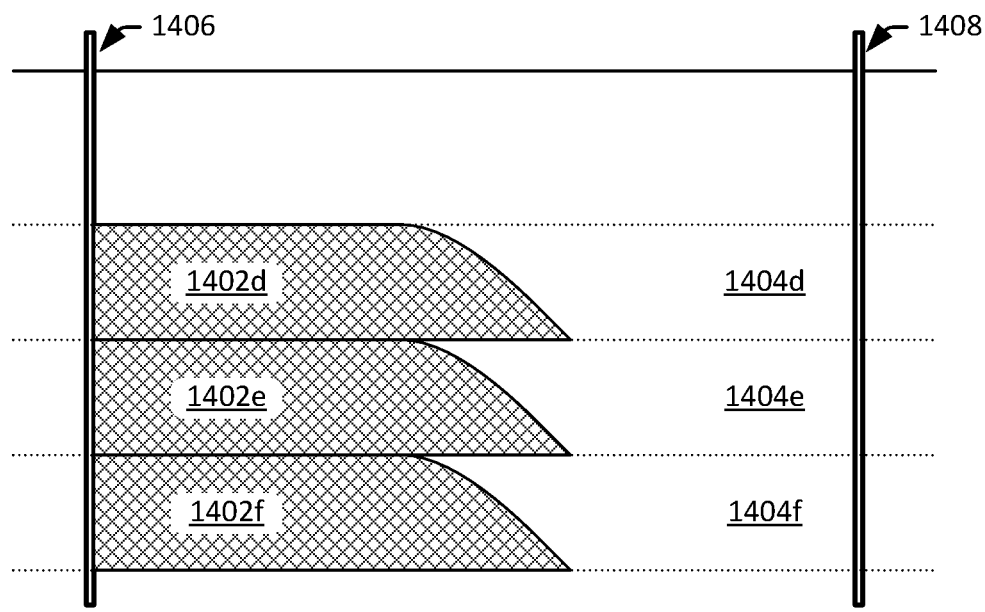
FIG. 14B is a diagram that illustrates relatively even advancement of flood front saturation profiles in multiple reservoir layers.

FIG. 14B is a diagram that illustrates relatively even advancement of flood front saturation profiles in multiple reservoir layers in accordance with one or more embodiments. In the illustrated embodiment, the first, second, and third flood front saturation profile 1402d, 1402e and 1402f indicate that injected fluid (indicated by the shaded area) is advancing (e.g., from the injection location, such as the injection well 1406, to the production location, such as the production well 1408) at about the same rate (e.g., having rates within about 10% of one another) in the first/upper layer 1404d, the second/middle layer 1404e, and the third/lower layer 1404f.

The embodied techniques have been sufficiently described so that a person with average knowledge in the matter may reproduce and obtain the results described here. Nonetheless, any skilled person in the field of technique, subject of the described embodiments , may carry out modifications not described, to apply these modifications to a determined structure, or in the manufacturing process of the same, requires the claimed matter in the following claims; such structures shall be covered within the scope of the described embodiments.

It should be noted and understood that there can be improvements and modifications made of the described embodiments without departing from the spirit or scope of the described embodiments as set forth in the accompanying claims.

As used throughout this application, the word "may" is used in a permissive sense (i.e., meaning having the potential to), rather than the mandatory sense (i.e., meaning must). The words "include," "including," and "includes" mean including, but not limited to. As used throughout this application, the singular forms "a", "an," and "the" include plural referents unless the content clearly indicates otherwise. Thus, for example, reference to "an element" may include a combination of two or more elements. As used throughout this application, the term "or" is used in an inclusive sense, unless indicated otherwise. That is, a description of an element including A or B may refer to the element including one or both of A and B. As used throughout this application, the phrase "based on" does not limit the associated operation to being solely based on a particular item. Thus, for example, processing "based on" data A may include processing based at least in part on data A and based at least in part on data B, unless the content clearly indicates otherwise. As used throughout this application, the term "from" does not limit the associated operation to being directly from. Thus, for example, receiving an item "from" an entity may include receiving an item directly from the entity or indirectly from the entity (e.g., by way of an intermediary entity). Unless specifically stated otherwise, as apparent from the discussion, it is appreciated that throughout this specification discussions utilizing terms such as "processing," "computing," "calculating," "determining," or the like refer to actions or processes of a specific apparatus, such as a special purpose computer or a similar special purpose electronic processing/computing device. In the context of this specification, a special purpose computer or a similar special purpose electronic processing/computing device is capable of manipulating or transforming signals, typically represented as physical, electronic or magnetic quantities within memories, registers, or other information storage devices, transmission devices, or display devices of the special purpose computer or similar special purpose electronic processing/computing device.

What is claimed is:

1. A method of injecting fluid into different layers of a hydrocarbon reservoir, comprising:
for each of a first layer of the hydrocarbon reservoir and a second layer of the hydrocarbon reservoir:
partitioning a length of a sample of formation rock of the hydrocarbon reservoir into a given number of length increments;
determining, for a selected time increment, fluid saturations of the length increments based on fluid injected into the length of the sample comprising:
for each length increment of the length increments:
determining a volume of fluid injected into the length increment of the sample during the selected time increment;
determining fractional flow of fluid produced from the length increment of the sample by the fluid injected into the length increment of the sample during the selected time increment; and
determining a fluid saturation for the length increment attributable to the fractional flow of fluid produced and the fluid injected that is saturated into the length increment of the sample during the selected time increment;
determining, based on the fluid saturations of the length increments of the sample during the selected time increment, whether the volume of the fluid injected is saturated into the length of the sample during the selected time increment; and
in response to determining that the volume of the fluid injected is saturated into the length of the sample during the selected time increment:
determining, based on the fluid saturations determined, a flood front saturation profile for the layer of the hydrocarbon reservoir;
determining a fluid injection rate for the layer that corresponds to the flood front saturation profile for the hydrocarbon reservoir; and
in response to determining the fluid injection rate for the first layer and the fluid injection rate for the second layer:
operating an injection well to inject fluid into the first layer of the reservoir at the fluid injection rate determined for the first layer; and
operating an injection well to inject fluid into the second layer of the reservoir at the fluid injection rate determined for the second layer.

2. The method of claim 1, wherein the fluid injection rate corresponds to the volume of fluid injected into the length increment of the sample during the selected time increment.

3. The method of claim 1, wherein the sample of formation rock of the hydrocarbon reservoir comprises a core sample extracted from the hydrocarbon reservoir.

4. The method of claim 1, wherein the injected fluid comprises water.

5. The method of claim 1, further comprising, in response to determining that the volume of the fluid injected is not saturated into the length of the sample during a selected time increment, determining, for a second time increment, second fluid saturations of the length increments based on fluid injected into the length of the sample for a second selected time increment, wherein the flood front saturation profile for the hydrocarbon reservoir is determined based on the second fluid saturations.

6. A non-transitory computer readable storage medium comprising program instructions stored thereon that are executable by a processor to cause the following operations for injecting fluid into different layers of a hydrocarbon reservoir:
for each of a first layer of the hydrocarbon reservoir and a second layer of the hydrocarbon reservoir:
partitioning a length of a sample of formation rock of the layer of the hydrocarbon reservoir into a given number of length increments;
determining, for a selected time increment, fluid saturations of the length increments based on fluid injected into the length of the sample comprising:
for each length increment of the length increments:
determining a volume of fluid injected into the length increment of the sample during the selected time increment;
determining fractional flow of fluid produced from the length increment of the sample by the fluid injected into the length increment of the sample during the selected time increment; and
determining a fluid saturation for the length increment attributable to the fractional flow of fluid produced and the fluid injected that is saturated into the length increment of the sample during the selected time increment;
determining, based on the fluid saturations of the length increments of the sample during the selected time increment, whether the volume of the fluid injected is saturated into the length of the sample during the selected time increment; and
in response to determining that the volume of the fluid injected is saturated into the length of the sample during the selected time increment:
determining, based on the fluid saturations determined, a flood front saturation profile for the layer of the hydrocarbon reservoir;
determining a fluid injection rate for the layer that corresponds to the flood front saturation profile for the layer of the hydrocarbon reservoir; and
in response to determining the fluid injection rate for the first layer and the fluid injection rate for the second layer:
operating an injection well to inject fluid into the first layer of the reservoir at the fluid injection rate determined for the first layer; and
operating an injection well to inject fluid into the second layer of the reservoir at the fluid injection rate determined for the second layer.

7. The medium of claim 6, wherein the fluid injection rate corresponds to the volume of fluid injected into the length increment of the sample during the selected time increment.

8. The medium of claim 6, wherein the sample of formation rock of the hydrocarbon reservoir comprises a core sample extracted from the hydrocarbon reservoir.

9. The medium of claim 6, wherein the injected fluid comprises water.

10. The medium of claim 6, the operations further comprising, in response to determining that the volume of the fluid injected is not saturated into the length of the sample during a selected time increment, determining, for a second selected time increment, second fluid saturations of the length increments based on fluid injected into the length of the sample for a second time increment, wherein the flood front saturation profile for the hydrocarbon reservoir is determined based on the second fluid saturations.

11. A system for injecting fluid into different layers of a hydrocarbon reservoir, the system comprising:
a reservoir flood front simulation system configured to:
for each of a first layer of the hydrocarbon reservoir and second layer of the hydrocarbon reservoir:
partition a length of a sample of formation rock of the layer of the hydrocarbon reservoir into a given number of length increments;
determine, for a selected time increment, fluid saturations of the length increments based on fluid injected into the length of the sample comprising:
for each length increment of the length increments:
determining a volume of fluid injected into the length increment of the sample during the selected time increment;
determining fractional flow of fluid produced from the length increment of the sample by the fluid injected into the length increment of the sample during the selected time increment; and
determining a fluid saturation for the length increment attributable to the fractional flow of fluid produced and the fluid injected that is saturated into the length increment of the sample during the selected time increment;
determine, based on the fluid saturations of the length increments of the sample during the selected time increment, whether the volume of the fluid injected is saturated into the length of the sample during the selected time increment; and
in response to determining that the volume of the fluid injected is saturated into the length of the sample during the selected time increment:
determine, based on the fluid saturations determined, a flood front saturation profile for the layer of the hydrocarbon reservoir; and
determine a fluid injection rate for the layer that corresponds to the flood front saturation profile for the hydrocarbon reservoir; and
an injection well system comprising an injection well configured to:
inject fluid into the first layer of the reservoir at the fluid injection rate determined for the first layer responsive to the determination of the fluid injection rate for the first layer by the reservoir flood front simulation system; and
inject fluid into the second layer of the reservoir at the fluid injection rate determined for the second layer responsive to the determination of the fluid injection rate for the second layer by the reservoir flood front simulation system.

12. The system of claim 11, wherein the fluid injection rate corresponds to the volume of fluid injected into the length increment of the sample during the selected time increment.

13. The system of claim 11, wherein the sample of formation rock of the hydrocarbon reservoir comprises a core sample extracted from the hydrocarbon reservoir.

14. The system of claim 11, wherein the injected fluid comprises water.

15. The system of claim 11, the reservoir flood front simulation system further configured to, in response to determining that the volume of the fluid injected is not saturated into the length of the sample during a selected time increment, determine, for a second selected time increment, second fluid saturations of the length increments based on fluid injected into the length of the sample for a second time increment, wherein the flood front saturation profile for the hydrocarbon reservoir is determined based on the second fluid saturations.

16. A method of injecting fluid into different layers of a hydrocarbon reservoir based on a model of fluid saturation as a function of length within a porous media segment of earth formation rock of a reservoir during flow through the porous media segment of a volume of a fluid injected into the porous media segment at an initial time to form immiscible oil and water fluid phases, the method comprising the steps of:
for each of a first layer of the hydrocarbon reservoir and a second layer of the hydrocarbon reservoir:
(a) partitioning a length of a sample of the porous media segment of the layer into a number of sample length increments;
(b) forming a measure of a volume of water injected into a sample length increment during a selected time increment;
(c) forming a measure of fractional flow of fluid produced in the sample length increment of the porous media segment by the injected water during the selected time increment;
(d) forming a measure of the fluid saturation for the injected water in the sample length increment of the porous media segment during the selected time increment;
(e) forming a record of the measure of the fractional flow of fluid produced and the measure of the fluid saturation for the injected water in the sample length increment of the porous media segment during the selected time increment;
(f) forming a measure of the remaining volume of the injected water not saturated into the sample length increment of the porous media segment during the selected time increment;
(g) determining whether measures of the fluid saturation for the injected water have been formed for each sample length increment of the porous media segment during the selected time increment, and
(h) if not, selecting a next adjacent sample length increment of the porous media segment during the selected time increment, and returning to the steps of forming a measure of the fractional flow of fluid produced and forming a measure of the fluid saturation for the injected fluid for the next adjacent sample length increment of the porous media segment;
(i) and, if so, determining whether the formed measure of remaining volume of the injected water during the selected time increment indicates presence of a remaining volume of water for injection into an adjacent length sample increment of the porous media segment;

(j) if so, incrementing the selected time increment to a new selected time increment and repeating the steps of forming a measure of fractional flow of fluid, forming a measure of the fluid saturation, forming a record of the measure of the of the fluid saturation, and forming a measure of the remaining volume of the injected water not saturated for injection into the adjacent sample length increment of the porous media segment during the selected time increment; and (k) if not, modeling the fluid saturation for the injected water for the layer as a function of the length of the porous media segment in response to the volume of water injected, results of the modeling of the fluid saturation indicating different flow rate behavior of the immiscible oil and water phases during the injecting of water into the porous media segment of the layer; and (l) determining a fluid injection rate for the layer that corresponds to the modeling of the fluid saturation; and operating an injection well system to:
  inject fluid into the first layer of the reservoir at the fluid injection rate determined for the first layer responsive to the determination of the fluid injection rate for the first layer; and
  inject fluid into the second layer of the reservoir at the fluid injection rate determined for the second layer responsive to the determination of the fluid injection rate for the second layer.

* * * * *

UNITED STATES PATENT AND TRADEMARK OFFICE
CERTIFICATE OF CORRECTION

Page 1 of 1

PATENT NO. : 11,066,911 B2
APPLICATION NO. : 16/186151
DATED : July 20, 2021
INVENTOR(S) : Mohammed Jawad A. Alshakhs It is certified that error appears in the above-identified patent and that said Letters Patent is hereby corrected as shown below:

In the Claims

In Column 23, Claim 11, Line 56 should read:
-- an injection well system configured to: --

Signed and Sealed this
Twenty-fourth Day of August, 2021

Drew Hirshfeld
*Performing the Functions and Duties of the*
*Under Secretary of Commerce for Intellectual Property and*
*Director of the United States Patent and Trademark Office*